US00PP30677P2

(12) United States Plant Patent
Smith

(10) Patent No.: US PP30,677 P2
(45) Date of Patent: Jul. 9, 2019

(54) ***CHRYSANTHEMUM* PLANT NAMED 'CIFZ0066'**

(50) Latin Name: ***Chrysanthemum* x *morifolium***
Varietal Denomination: CIFZ0066

(71) Applicant: SYNGENTA PARTICIPATIONS AG, Basel (CH)

(72) Inventor: Mark A. Smith, Alva, FL (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/932,544

(22) Filed: Mar. 13, 2018

(51) Int. Cl.
*A01H 5/02* (2018.01)
*A01H 6/14* (2018.01)

(52) U.S. Cl.
USPC ..... Plt./297

(58) Field of Classification Search
USPC ..... Plt./263.1, 284, 287, 297
See application file for complete search history.

*Primary Examiner* — Susan McCormick Ewoldt
*Assistant Examiner* — Karen M Redden
(74) *Attorney, Agent, or Firm* — Dale Skalla

(57) ABSTRACT

A new garden type *Chrysanthemum* plant named 'CIFZ0066' particularly distinguished by a medium sized plant with upright to outwardly spreading and uniform mounded plant habit, 4-4.5 cm dark pink daisy flowers and a natural season response in late September to early October.

1 Drawing Sheet

Latin name of the genus and species of the plant claimed: *Chrysanthemum* x *morifolium*.

Varietal denomination: 'CIFZ0066'.

BACKGROUND OF THE NEW PLANT

The present invention comprises a new *Chrysanthemum*, botanically known as *Chrysanthemum* x *morifolium*, and hereinafter referred to by the variety name 'CIFZ0066'.

'CIFZ0066' is a product of a planned breeding program. The new cultivar has a medium size plant with upright to outwardly spreading and uniform mounded plant habit, 4-4.5 cm dark pink daisy flowers and a natural season response in late September to early October.

'CIFZ0066' originated from a mutation: Stock x-rayed at 1750 RAD in October of 2012. The variety was found as a single cutting sport from the stock.

The female parent was 'Jacqueline Pink Improved', 'CIFZ0015', U.S. Plant Pat. No. 25,905. When compared to the female parent, 'CIFZ0066' has:

1) Similar flower type and a similar to a bit larger flower size but more coral/less lavender color than the sport parent
2) Blackcloth is 2 days faster and natural season response is 3 days faster than the sport parent
3) Similar plant habit with similar to a bit smaller plant size than the sport parent No male parent.

The first act of asexual reproduction of 'CIFZ0066' was accomplished when vegetative cuttings were propagated from the initial selection, this initial selection took place on Apr. 9, 2013 in Gilroy, Calif.

BRIEF SUMMARY OF INVENTION

Horticultural examination of plants grown from cuttings of the plant initiated in May, 2013 in Gilroy, Calif., and continuing thereafter, has demonstrated that the combination of characteristics as herein disclosed for 'CIFZ0066' are firmly fixed and are retained through successive generations of asexual reproduction.

'CIFZ0066' has not been observed under all possible environmental conditions. The phenotype may vary significantly with variations in environment such as temperature, light intensity and day length.

A Plant Breeder's Right for this cultivar has not been applied for. 'CIFZ0066' has not been made publicly available prior to the effective filing date of this application, notwithstanding any disclosure that may have been made less than one year prior to the effective filing date of this application by the inventor or another who obtained 'CIFZ0066' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0066' with colors being as true as possible with an illustration of this type.

Figure 1:
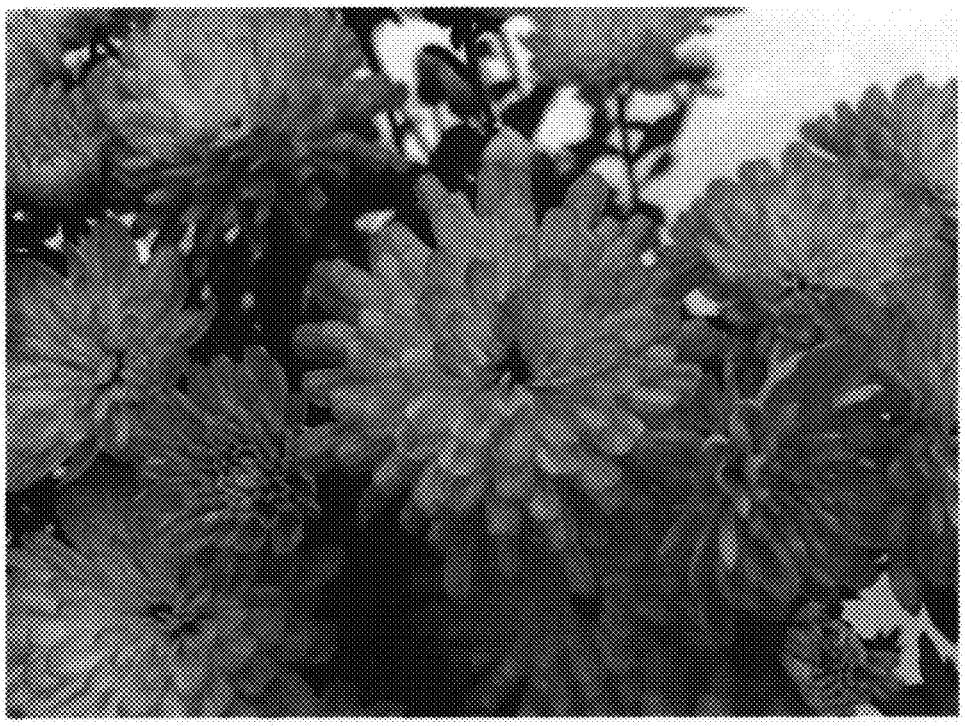
Figure 2:
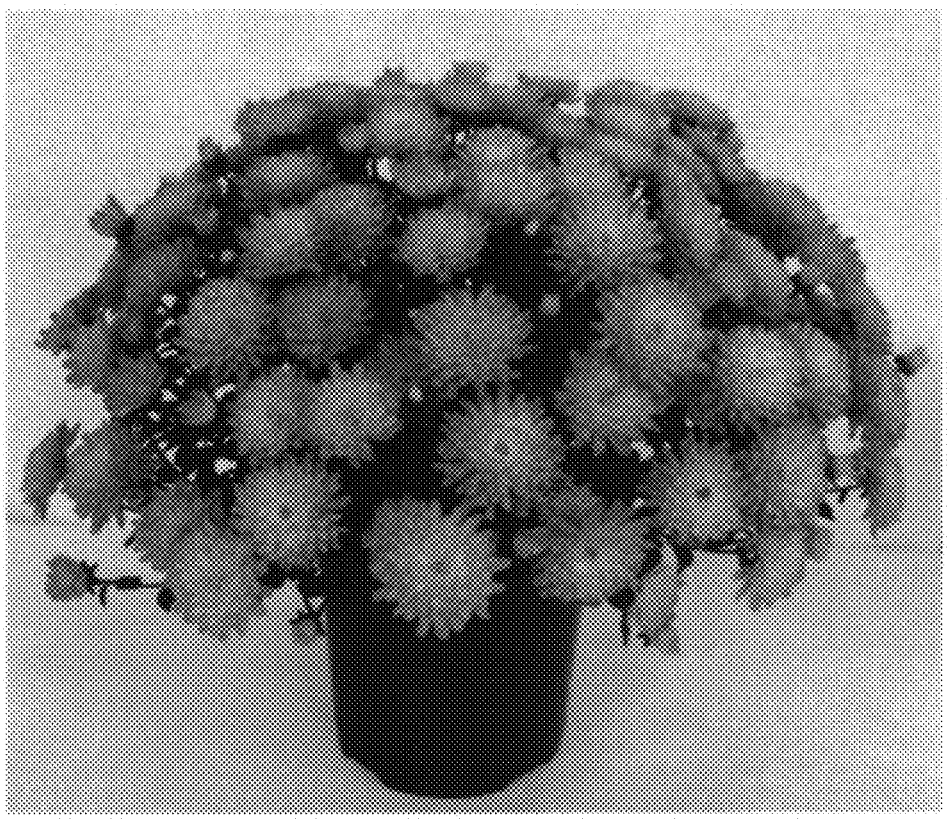

The photographic drawings show in FIG. 1 a close view of flower of the new variety and in FIG. 2 a flowering plant from an outdoor trial.

The aforementioned photographs: FIG. 1 and FIG. 2 were taken in August 2017 both showing a plant from the same blackcloth indoor trial in Gilroy, Calif. These plants were about 10 weeks of age. One rooted cutting per pot had been planted in a one gallon pot, not pinched in week 24, and black clothed from week 25. Plants started flowering in August.

DETAILED BOTANICAL DESCRIPTION

The measurements were taken in Gilroy, Calif. in August 2017 on the plants from the aforementioned trial.

Color references are made to The Royal Horticultural Society Colour Chart (R.H.S.) 2001.

TABLE 1

DIFFERENCES BETWEEN THE NEW VARIETY 'CIFZ0066' AND TWO MOST SIMILAR VARIETIES:

| | 'CIFZ0066' | 'Synjac Peafus', U.S. Plant Pat. No. 22,655 ('Jacqueline Peach Fusion') |
|---|---|---|
| Flowering response (blackcloth): | 1 day faster | 1 day slower |
| Flower shape: | Similar flower type with similar or a bit larger size and stronger flower color that holds better in warmer temperatures | Similar flower type with similar or a bit smaller size and more pale flower color that does not hold in warmer temperatures |
| Plant habit or size: | Similar plant size and plant habit | Similar plant size and plant habit |
| | 'CIFZ0066' | 'Fiorra Pink', U.S. Plant Pat. No. 26,462 |
| Flowering response (natural): | Three weeks faster response | 3 weeks slower response |
| Plants, stems, flexibility: | Flexible stems | Stems can break easily when compressed |
| Plant habit or size: | Similar overall size but rounder/more ball shaped (height more similar to width)/less mound shaped (height smaller than width) | Similar overall size but more mounded type |

Plant:

*Form, growth and habit.*—Herbaceous garden-type, freely branching, strong and moderately vigorous, upright to outwardly spreading and uniform mounded growth habit.

*Plant height (above soil).*—15-18 cm.

*Plant height (inflorescence included).*—16-20 cm.

*Plant width.*—30-35 cm.

Roots:

*Number of days to initiate roots.*—About 4 days at about 22° C.

*Number of days to produce a rooted cutting.*—14-16 days at 22° C.

*Type.*—Fine, fibrous, free branching.

*Color.*—RHS N155B but whiter.

Foliage:

*Arrangement.*—Alternate.

*Immature leaf, color upper surface.*—RHS 139A.

*Immature leaf, color lower surface.*—RHS N138A.

*Mature leaf, color, upper surface.*—Closest to 136B.

*Mature leaf, color lower surface.*—RHS 138B.

*Length.*—2.9-3.9 cm.

*Width.*—2.5-3.0 cm.

*Shape.*—Ovate, with distinct lobes.

*Base shape.*—Attenuate.

*Apex shape.*—Mucronate.

*Margin.*—5-lobed (palmate), edge dentate.

*Upper surface.*—Bifid hairs.

*Lower surface.*—Bifid hairs.

*Color of veins, upper surface.*—RHS 138B.

*Color of veins, lower surface.*—RHS N138B.

*Pattern of veining.*—Palmate.

*Petiole color.*—RHS 138A.

*Petiole length.*—0.9-1.8 cm.

*Diameter.*—0.2 cm.

*Hairs.*—Bifid hairs.

Stem:

*Quantity of main branches per plant.*—5-7.

*Color of stem.*—RHS 138A.

*Length of stem.*—5.5-7.0 cm.

*Diameter.*—0.5 cm.

*Length of internodes.*—0.5-1.7 cm.

*Hairs.*—Bifid hairs.

*Color of peduncle.*—RHS 138A.

*Length of peduncle.*—4.6-7.8 cm.

*Peduncle diameter.*—0.1-0.15 cm.

*Hairs.*—Bifid hairs.

Inflorescence:

*Type.*—Compositae, solitary, decorative-type inflorescences borne terminally above foliage, ligulate ray florets arranged acropetally on a capitulum giving a double flower.

*Quantity of short days to flowering (response time).*—Approximately 6 weeks.

*Natural season flowering.*—Late September to early October.

*Quantity of inflorescences per plant.*—60-80, with many small buds developing.

*Lastingness of individual blooms on the plant.*—About five weeks from first color.

*Fragrance.*—Slightly spicy.

Bud (when showing color):

*Color.*—Closest to RHS 160A; RHS 60A bleeding through at apex.

*Length.*—1.0-1.2 cm.

*Width.*—1.0-1.3 cm.

*Shape.*—Oblate.

Immature inflorescence:

*Diameter.*—3.0-3.5 cm.

*Color of ray florets, upper surface.*—RHS 2C, overlain with light layer of RHS 64B; darkest at apex.

*Color of ray florets, lower surface.*—RHS 2C with RHS 64B at apical margin.

Mature inflorescence:

*Diameter.*—4.0-4.5 cm.

*Depth.*—1.3-1.5 cm.

*Total diameter of disc.*—0.3 cm to no disk present.

*Receptacle color.*—RHS 144A.

*Receptacle height.*—0.2 cm.

*Receptacle diameter.*—3.0 cm.

Ray florets:

*Average quantity of florets.*—Between 130 and 150 in several whorls.

*Color of florets, upper surface (abaxial).*—Outer layers; RHS 1D overlain with RHS 64B; darker at apex.

*Color inner surface (adaxial).*—RHS 1D with RHS 64B at margin.

*Length.*—1.8-2.1 cm.

*Width/diameter.*—0.4-0.5 cm.

*Shape.*—Elliptical.

*Apex shape.*—Mostly obtuse and dentate.

*Base shape.*—Tube.

*Margin.*—Entire. Small incisions may be present at tip.

*Texture, upper surface.*—Papillate.

*Lower surface.*—Papillate.

Disc florets: Up to 200, may not be present in all flowers.

*Width.*—Up to 0.5 cm.

*Length.*—3.0 cm.

*Colour.*—RHS 1B; 144B at base.

Phyllaries:

*Quantity.*—20-25.
*Color, upper surface.*—RHS 137A.
*Color, lower surface.*—RHS 137A.
*Length.*—0.5 cm.
*Width.*—0.1 cm.
*Shape.*—Lanceolate.
*Apex shape.*—Acute.
*Base.*—Fused.
*Margins.*—Entire.
*Texture, upper surface.*—Glabrous.
*Texture, lower surface.*—Canescent.

Reproductive organs:

*Pistil.*—One.
*Length.*—0.2-0.5 cm.
*Style color.*—RHS 150A.
*Style length.*—0.4 cm.
*Stigma color.*—RHS 7D.
*Stigma shape.*—Bi-parted.
*Ovary color.*—RHS 145C.
*Ovary length.*—0.2 cm.
*Ovary width.*—0.1 cm.

Androecium:

*Stamens.*—1, found on only disc florets.
*Color of filaments.*—RHS 2B.
*Length filaments.*—0.2 cm.
*Anther color.*—RHS 13A.
*Anther length.*—0.2 cm.
*Anther shape.*—Oval to club shaped.
*Color of pollen.*—RHS 13A.
*Pollen amount.*—Moderate.
*Fertility/seed set.*—Has not been determined to date.
*Disease/pest resistance.*—Has not been determined to date.
*Winter hardiness/cold tolerance.*—Has not been observed to date.
*Drought/heat tolerance.*—Has not been observed to date.

What is claimed is:

1. A new and distinct variety of *Chrysanthemum* plant named 'CIFZ0066' substantially as illustrated and described herein.

* * * * *